United States Patent
Avery et al.

(10) Patent No.: US 9,061,110 B2
(45) Date of Patent: Jun. 23, 2015

(54) CODED DRUG RESERVOIR CONNECTION ELEMENT WITH BENDABLE LOCKING ELEMENTS

(75) Inventors: Richard James Vincent Avery, Chipping Campden (GB); Aled Meredydd James, Dorridge (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 80 days.

(21) Appl. No.: 13/639,387

(22) PCT Filed: Apr. 7, 2011

(86) PCT No.: PCT/EP2011/055394
§ 371 (c)(1),
(2), (4) Date: Jan. 18, 2013

(87) PCT Pub. No.: WO2011/124631
PCT Pub. Date: Oct. 13, 2011

(65) Prior Publication Data
US 2013/0204201 A1    Aug. 8, 2013

Related U.S. Application Data

(60) Provisional application No. 61/322,702, filed on Apr. 9, 2010.

(30) Foreign Application Priority Data

Jul. 29, 2010   (EP) ..................................... 10171159

(51) Int. Cl.
*A61M 5/50*      (2006.01)
*A61M 5/24*      (2006.01)
*A61J 1/14*      (2006.01)

(52) U.S. Cl.
CPC ..... *A61M 5/5086* (2013.01); *A61M 2005/2403* (2013.01); *A61J 1/1406* (2013.01);
(Continued)

(58) Field of Classification Search
CPC .............. A61M 39/1011; A61M 2039/1077; A61M 2005/24; A61M 2005/2403; A61M 2005/2481; A61M 2005/2485; A61M 2005/2488; A61M 2005/2492; A61M 5/28; A61M 2005/2407; A61M 2005/244; A61J 1/00; A61J 1/1406; A61J 1/1412; A61J 1/1437; A61J 2001/1481; A61J 1/1475
USPC .......................................... 604/200, 244, 533
See application file for complete search history.

(56) References Cited

U.S. PATENT DOCUMENTS 3,865,353 A * 2/1975 Fischer ........................... 366/98
4,614,267 A   9/1986 Larkin
(Continued)

FOREIGN PATENT DOCUMENTS

EP   1034772   9/2000
EP   1930038   6/2008
(Continued)

OTHER PUBLICATIONS

International Search Report for Int. App. No. PCT/EP2011/055394, completed Jul. 11, 2011.
(Continued)

*Primary Examiner* — Quynh-Nhu H Vu
(74) *Attorney, Agent, or Firm* — McDonnell Boehnen Hulbert & Berghoff LLP (57) ABSTRACT

A locking mechanism is provided for use with a reservoir and a reservoir holder so as to prevent unwanted tampering with the reservoir. The mechanism comprises a main body that is coupled to the reservoir. A first bendable feature is provided on the main body. The first bendable feature snaps from a first position to a second position. In the second position, at least a portion of the bendable feature retains the reservoir within the locking mechanism.

11 Claims, 6 Drawing Sheets (52) U.S. Cl.
CPC ....... *A61J 1/1475* (2013.01); *A61J 2001/1481* (2013.01); *A61J 2205/40* (2013.01); *A61M 5/24* (2013.01); *A61M 2005/2407* (2013.01); *A61M 2005/244* (2013.01); *A61M 2205/276* (2013.01); *A61M 2205/6045* (2013.01)

(56) References Cited

U.S. PATENT DOCUMENTS

| | | | | |
|---|---|---|---|---|
| 5,334,162 | A | * | 8/1994 | Harris .......................... 604/232 |
| 5,554,134 | A | | 9/1996 | Bonnichsen |
| 6,688,654 | B2 | * | 2/2004 | Romero ....................... 285/308 |
| 8,500,173 | B2 | * | 8/2013 | Zahler et al. ................. 285/317 |
| 8,579,868 | B2 | * | 11/2013 | Christiansen ................ 604/211 |
| 2003/0004466 | A1 | | 1/2003 | Bitdinger et al. |
| 2003/0078195 | A1 | * | 4/2003 | Kristensen et al. ............... 514/3 |
| 2003/0153895 | A1 | * | 8/2003 | Leinsing ....................... 604/403 |
| 2004/0150223 | A1 | * | 8/2004 | Campau ....................... 285/308 |
| 2004/0204715 | A1 | * | 10/2004 | Evans et al. ..................... 606/92 |
| 2005/0137566 | A1 | * | 6/2005 | Fowles et al. ................. 604/412 |
| 2005/0225082 | A1 | * | 10/2005 | Dalle et al. .................... 285/330 |
| 2006/0025751 | A1 | * | 2/2006 | Roy et al. ..................... 604/523 |
| 2010/0218846 | A1 | * | 9/2010 | Kriheli ............................. 141/5 |

FOREIGN PATENT DOCUMENTS

| | | |
|---|---|---|
| WO | 03/047667 | 6/2003 |
| WO | 2008/071804 | 6/2008 |

OTHER PUBLICATIONS

International Preliminary Report on Patentability for Int. App. No. PCT/EP2011/055394, mailed Jun. 12, 2012.

* cited by examiner

CODED DRUG RESERVOIR CONNECTION ELEMENT WITH BENDABLE LOCKING ELEMENTS

CROSS REFERENCE TO RELATED APPLICATIONS

The present application is a U.S. National Phase Application pursuant to 35 U.S.C. §371 of International Application No. PCT/EP2011/055394 filed Apr. 7, 2011, which claims priority to U.S. Provisional Patent Application No. 61/322,702 filed Apr. 9, 2010 and European Patent Application No. 10171159.6 filed Jul. 29, 2010. The entire disclosure contents of these applications are herewith incorporated by reference into the present application.

FIELD OF INVENTION

The present patent application is generally directed to reservoirs, particularly reservoirs containing a medicament. More particularly, the present application is generally directed to a locking mechanism for use with a reservoir and a reservoir holder so as to prevent unwanted reservoir tampering. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user simply loads a new cartridge into the delivery system without the drug delivery device or without the cartridge having any mechanism of preventing removal and subsequent cross use of an incorrect cartridge. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and must comply with certain recognized local and international standards. Consequently, such cartridges are typically supplied in standard sized cartridges (e.g., 3 ml cartridges). Therefore, there may be a variety of cartridges supplied by a number of different suppliers and containing different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate a cartridge to its drug type and design an injection device that is non-removably retained in a locking mechanism so as to prevent unwanted cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products.

SUMMARY

It is an object of the present invention to facilitate the correct application of a drug reservoir to a drug delivery device.

This object is achieved by the locking mechanism according to claim 1 and the drug delivery system according to claim 6, respectively. Embodiments derive from the dependent claims.

In the following the term "distal end" refers to a part of the cartridge assembly or of a body or housing which is intended to be arranged at a portion of a drug delivery device from which a drug is dispensed. The term "proximal end" refers to a part of the cartridge assembly or of the body or housing which is remote from the distal end. The term "distal direction" refers to a movement in the same direction as a movement from the proximal end towards the distal end, not specifying a point of departure nor an end point, so that the movement may go beyond the distal end. The term "proximal direction" refers to a movement in the direction opposite to the distal direction.

In one aspect, a locking mechanism for attaching a reservoir within a reservoir holder comprises a cylindrically shaped main body having an outer diameter and a centrally located aperture. At least one bendable feature is provided on the main body. The bendable feature is movable from a first position, in which at least a portion of the bendable feature extends beyond the outer diameter of the main body, to a second position, the portion moving toward aperture until the bendable feature snaps into the second position. In the second position, at least a portion of the bendable feature is provided to retain the reservoir within the locking mechanism.

According to an exemplary arrangement, a locking mechanism for attaching a reservoir within a reservoir holder comprises a main body coupled to the reservoir. A first bendable feature is provided on the main body. The bendable feature may be moved from a first position to a second position. To move the bendable feature from the first position to the second position, the bendable feature is pressed toward the reservoir. In the second position, at least a portion of the bendable feature retains the reservoir within the locking mechanism.

In another aspect, a drug delivery system comprises a drug delivery device with a dose setting member, a cartridge holder secured to the dose setting member, a cartridge contained within the cartridge holder, and a locking mechanism affixed to the cartridge. The locking mechanism comprises a cylindrically shaped main body having an outer diameter and a centrally located aperture and at least one bendable feature provided on the main body. The bendable feature is movable from a first position, in which at least a portion of the bendable feature extends beyond the outer diameter of the main body, to a second position, the portion moving toward aperture until the bendable feature snaps into the second position. In the second position, at least a portion of the bendable feature is provided to retain the reservoir within the locking mechanism.

In a drug delivery system comprising a drug delivery device a cartridge holder is secured to a dose setting member, which may comprise a dose setting mechanism.

In yet another alternative arrangement, a drug delivery system comprises a drug delivery device comprising a dose setting mechanism. A cartridge holder is secured to the dose setting mechanism. A cartridge is contained within the cartridge holder and a locking mechanism affixes to the cartridge. The locking mechanism may comprise a first bendable feature that snaps from a first position to a second position, the second position comprising at least a portion of said first bendable feature that prevents the return of the bendable feature to the first position.

In an embodiment of the locking mechanism the bendable feature is essentially concave to the reservoir when the reservoir is coupled to the main body and the bendable feature is in the first position.

In a further embodiment of the locking mechanism the bendable feature does not touch the reservoir when the bendable feature is in the first position.

In a further embodiment of the locking mechanism the bendable feature comprises a first section, a second section, and a third section.

In a further embodiment of the locking mechanism the first section and the third section are each affixed to the main body.

In a further embodiment of the locking mechanism the first section, the second section, and the third section are configured to form a generally rounded arc shape that, in said first position, radially extends away from the main body.

In a further embodiment of the locking mechanism the main body comprises a flange that extends along at least a portion of the perimeter of the main body.

In a further embodiment of the locking mechanism the main body is mounted on the reservoir, and the reservoir has a neck part that comprises a pierceable seal across the open distal end of the neck part.

A further embodiment of the locking mechanism comprises a thread configured for receiving a threaded needle hub.

A further embodiment of the locking mechanism is manually pressed from said first position to said second position during an assembly step.

A further embodiment of the locking mechanism further comprises a retention feature.

In a further embodiment of the locking mechanism the retention feature comprises a flange extending from the main body that mates with a groove in the reservoir holder.

A drug delivery system comprises a drug delivery device comprising a dose setting mechanism, a cartridge holder, wherein said cartridge holder is secured to said dose setting mechanism, a cartridge contained within the cartridge holder, and a locking mechanism affixed to the cartridge. The locking mechanism comprises a first bendable feature that snaps from a first position to a second position. The second position comprises at least a portion of the first bendable feature preventing the return of the bendable feature to the first position.

In an embodiment of the drug delivery system the locking mechanism further comprises a main body with an aperture extending through the center of the main body.

In a further embodiment of the drug delivery system the bendable feature is essentially concave to the aperture when the bendable feature is in the first position.

In a further embodiment of the drug delivery system the bendable feature comprises a first section, a second section, and a third section.

In a further embodiment of the drug delivery system the first section and the third section are each affixed to the main body.

In a further embodiment of the drug delivery system the first section, the second section, and the third section are configured to form a generally rounded arc shape that, in the first position, radially extends away from the main body.

In a further embodiment of the drug delivery system the main body comprises a flange that extends along at least a portion of the perimeter of the main body.

In a further embodiment of the drug delivery system the main body comprises a flange, and the locking mechanism further comprises an axially extending wall, which extends from the flange and includes a connector for connecting the locking mechanism to the dose setting member.

In a further embodiment of the drug delivery system an outer surface of the axially extending wall of the main body is provided with an outer thread.

In a further embodiment of the drug delivery system the locking mechanism comprises a non-return feature, the bendable feature moving from the first position past the non-return feature to the second position and being held in the second position by the non-return feature.

In a further embodiment of the drug delivery system the cartridge holder is removably secured to the dose setting mechanism.

In a further embodiment of the drug delivery system the cartridge is removably contained within the cartridge holder.

In a further embodiment of the drug delivery system the drug delivery device comprises a reusable drug delivery device.

In a further embodiment of the drug delivery system the dose setting mechanism comprises a rotating piston rod for expelling a set dose from the cartridge.

The term "drug" or "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B3) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative; or an Exendin-4 derivative of the sequence H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of the invention is defined by the content of the claims. The invention is not limited to specific embodiments but comprises any combination of elements of different embodiments. Moreover, the invention comprises any combination of claims and any combination of features disclosed by the claims.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described in the following description with reference to the drawings, in which.

DETAILED DESCRIPTION

Figure 1:
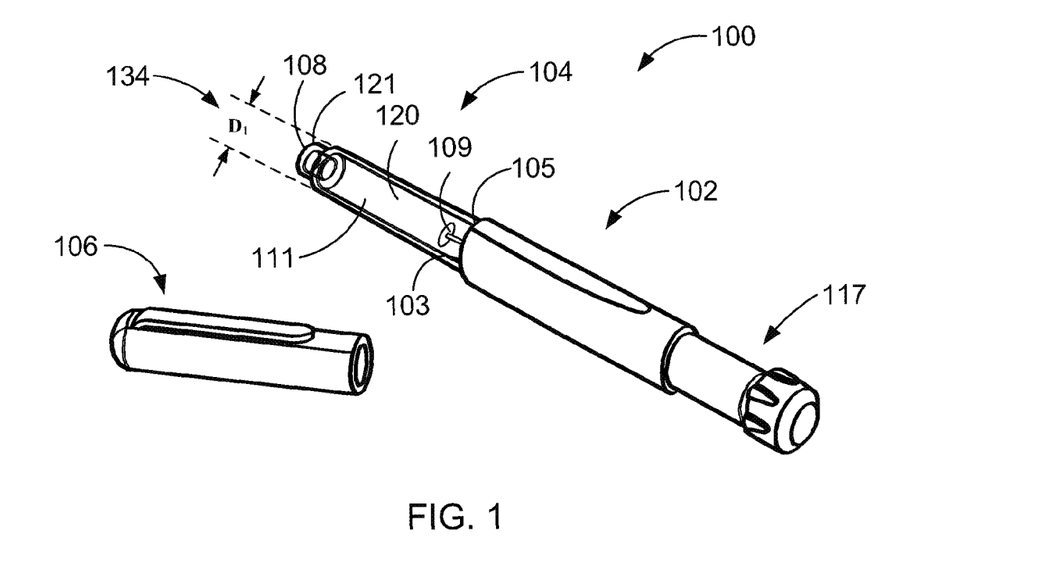
FIG. 1 illustrates an exemplary pen type drug delivery device.

Referring to FIG. 1, there is shown a drug delivery device 100 in the form of a pen type syringe. This drug delivery device 100 comprises a dose setting member 102, which may comprise a dose setting mechanism, a cartridge holder 104, and a removable cap 106. A proximal end 105 of the cartridge holder 104 and a distal end 103 of the dose setting member 102 are removably secured together. The pen type syringe may comprise a re-usable or a disposable pen type syringe. Where the syringe comprises a re-usable device, the cartridge holder 104 and the dose setting member 102 are removably coupled together. In a disposable device, they may be permanently coupled together. In FIG. 1, the dose setting member 102 comprises a piston rod 109, such as a threaded piston rod 109 that rotates when a dose is injected.

To inject a previously set dose, a double ended needle assembly may be attached to a distal end 108 of the cartridge holder 104. Preferably, the distal end 108 of the cartridge holder 104 comprises a thread 121 (or other suitable connecting mechanism such as a snap lock, snap fit, form fit, or bayonet lock mechanism) so that the needle assembly may be removably attached to the distal end 108 of the cartridge holder 104. When the drug delivery device 100 is not in use, the removable cap 106 can be releasably retained over the cartridge holder 104.

Figure 2:
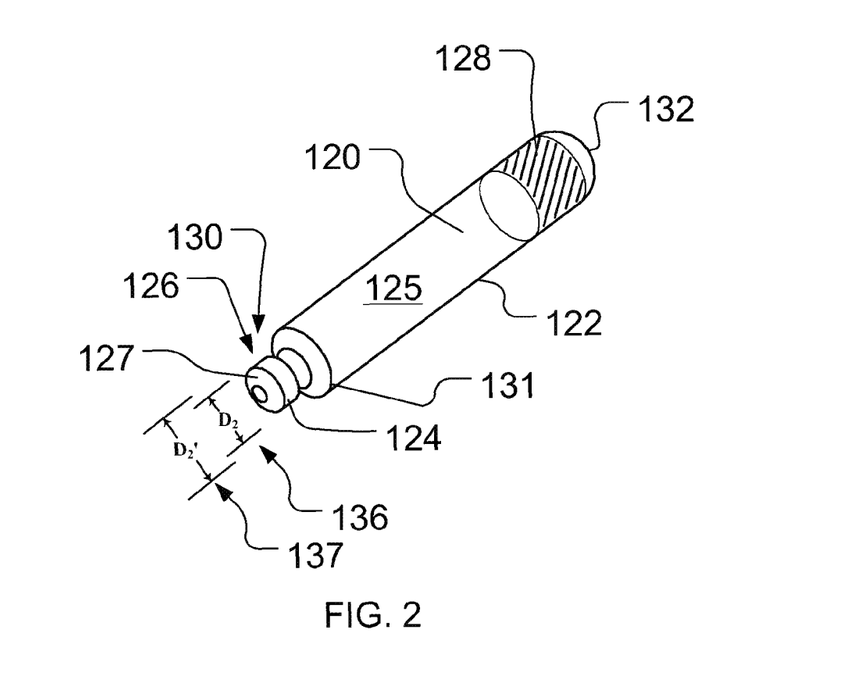
FIG. 2 illustrates a cartridge that may be loaded into a cartridge holder of the pen type drug delivery device illustrated in FIG. 1.

An inner cartridge cavity 111 defined by the cartridge holder 104 is dimensioned and configured to securely receive and retain the cartridge 120. FIG. 2 illustrates a perspective view of the cartridge 120 that may be used with the drug delivery device 100 illustrated in FIG. 1. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck 126 projects distally from the shoulder 131 of the barrel 122. Preferably, this smaller diameter neck 126 is provided with a large diameter annular bead (not shown) and this bead extends circumferentially thereabout at the extreme distal end of the neck 126. A pierceable seal or septum 127 is securely mounted across the open distal end defined by the neck 126. The seal or septum 127 may be held in place by a metallic sleeve or ferrule 124. This metallic sleeve or ferrule 124 may be crimped around the circumferential bead at the distal end of the neck 126. The diameter of the metallic sleeve or ferrule 124 is shown as diameter $D_2$ 136. The medicament 125 is pre-filled into the cartridge 120 and is retained within the cartridge 120, in part, by the pierceable seal or septum 127, the metallic sleeve or ferrule 124, and the stopper 128. The stopper 128 may be in sliding fluid-tight engagement with the inner tubular wall of the barrel 122. Axially directed forces acting upon the stopper 128 during dose injection or dose administration urge the medication 125 from the cartridge 120 though a double ended needle mounted onto the distal end 108 of the cartridge holder 104 and into the injection site. Such axial forces may be provided by the piston rod 109.

A portion of the cartridge holder 104 defining the cartridge cavity 111 is of substantially uniform diameter represented in FIG. 1 by diameter $D_1$ 134. This diameter $D_1$ 134 is preferably slightly greater than the diameter $D_2'$ 137 of the cartridge 120. The interior of the cartridge holder 104 includes an inwardly-extending annual portion or stop that is dimensioned to prevent the cartridge 120 from moving within the cartridge holder 104. In this manner, when the cartridge 120 is loaded into the cartridge cavity 111 of the cartridge holder 104 and the cartridge holder 104 is then connected to the dose setting member 102, the cartridge 120 will be securely held within the cartridge cavity 111. More particularly, the neck 126 and the metallic sleeve or ferrule 124 of the cartridge 120 are inserted in a distal direction into the open proximal end of the cartridge holder 104 with the metallic sleeve or ferrule 124 eventually passing entirely into the cartridge holder 104. With the cartridge holder 104 removably coupled to the dose setting member 102, the proximal end 132 of the cartridge 120 will typically abut a stop provided by the dose setting member 102.

A number of doses of a medicament 125 may be dispensed from the cartridge 120. The cartridge 120 may contain a type of medicament 125 that must be administered often, such as one or more times a day. One such medicament is insulin. The stopper 128 is retained in a first end or proximal end 132 of the cartridge 120 and receives an axial force created by the piston rod 109 of the dose setting mechanism that may be provided in the dose setting member 102.

The dose setting member 102 comprises a dose setter 117 at the proximal end of the dose setting member 102. In one preferred arrangement, the dose setter 117 is rotated to set a dose. To administer this set dose, the user may attach a needle assembly comprising a double ended needle on the distal end 108 of the cartridge holder 104. In this manner, the needle assembly pierces the seal or septum 127 of the cartridge 120 and is therefore in liquid communication with the medicament 125. The user pushes on the dose setter 117 to inject the set dose. The same dose setting and dose administration procedure may be followed until the medicament 125 in the cartridge 120 is expended, at which time a new cartridge 120 may be loaded in the device. To exchange an empty cartridge 120, the user is called upon to remove the cartridge holder 104 from the dose setting member 102.

Figure 3:
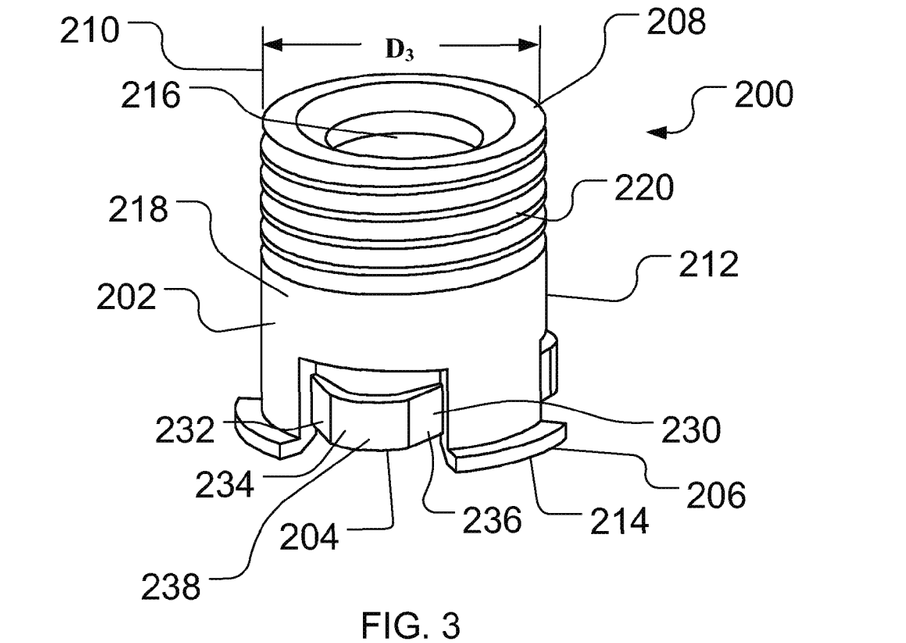
FIG. 3 illustrates a first arrangement of a locking mechanism for use with a cartridge that may be used with a pen type drug delivery device, such as the drug delivery device illustrated in FIG. 1.

FIG. 3 illustrates a first arrangement of a locking mechanism 200 for use with a cartridge that may be used with a pen type drug delivery device, such as the cartridge 120 illustrated in FIG. 2. More specifically, the locking mechanism 200 may comprise a flexible material that can be snapped over the distal end 130 of the cartridge 120 such that the locking mechanism 200 form fits or snaps around the metallic sleeve or ferrule 124 of the cartridge 120. In this manner, and as explained in greater detail below, the locking mechanism 200 can provide a locking feature to the cartridge 120. Alternatively, the locking mechanism 200 may comprise a non-flexible material so that it does not deform when positioned over the distal end 130 of the cartridge 120.

The locking mechanism 200 shown in FIG. 3 comprises a cylindrically shaped main body 202 defining a centrally located aperture 204. This aperture 204 extends from a proximal end 206 to a distal end 208 of the main body 202 and, when in use, the aperture 204 is placed over the ferrule 124 located at the distal end 130 of a cartridge 120. Preferably, this aperture 204 has a diameter $D_3$ 210 that is slightly larger than the diameter $D_2$ 136 of the metallic sleeve or ferrule 124 of the cartridge 120. The locking mechanism 200 further comprises an axially extending wall 212 that extends from a flange 214 located near the proximal end 206 of the main body 202. This axially extending wall 212 extends towards the distal end 208 of the main body 202. The axially extending wall 212 may vary, and may be as long or longer than the cartridge 120 when the cartridge 120 is inserted within the locking mechanism 200. In addition, the axially extending wall 212 may include a connector for connecting the locking mechanism 200 along with the cartridge 120 to a dose setting member 102 (i.e., the locking mechanism 200 may become part of the cartridge holder 104).

Near the distal end 208, the locking mechanism 200 is provided with a pass-through or opening 216. In one arrangement, this pass-through or opening 216 is sized or configured so that, when the locking mechanism 200 is snapped over the metallic sleeve or ferrule 124 of the cartridge 120, the pass-through or opening 216 will expose a portion of the metallic sleeve or ferrule 124 of the cartridge 120 and will provide access to at least a portion of the pierceable seal or septum 127 of the cartridge 120.

In one arrangement, locking mechanism 200 is intended for use with a standard double ended needle, wherein this needle comprises a hub having an internal thread. As such, an outer surface 218 of the axially extending wall 212 of the main body 202 is provided with an outer thread 220 that receives such a hub of the double ended needle. Such an outer thread 220 could comprise a single or a double start outer thread. In addition, when such double ended needle is mounted onto the locking mechanism 200, the piercing distal needle projects through the pass-through or opening 216 and into the pierceable seal or septum 127 of the cartridge 120. Alternatively, the locking mechanism 200 may be provided without the outer thread 220.

Figure 4:
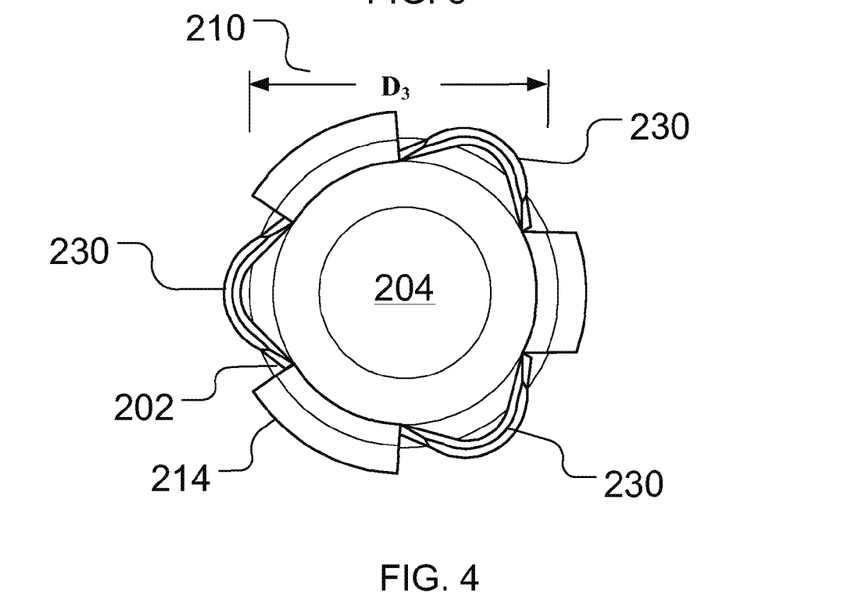
FIG. 4 illustrates a bottom view of a locking mechanism such as the locking mechanism illustrated in FIG. 3.

In this preferred arrangement, the locking mechanism 200 is provided with at least one bendable feature 230. Bendable feature 230 comprises an exterior surface 238. In one preferred arrangement, the bendable feature 230 may comprise a first section 232, a second section 234, and a third section 236. First section 232 and third section 236 are each affixed to main body 202. These three sections 232, 234, 236 of bendable feature 230 may be configured to form a generally rounded arc shape that, in a first position, radially extends away from the main body 202 so as to be essentially concave relative to the cartridge 120 when the cartridge 120 is inserted into the locking mechanism 200. The first position is the initial position of the locking mechanism 200 during assembly. In the first position, at least a portion of second section 234 of bendable feature 230 may extend beyond the outer diameter $D_3$ 210 of the main body 202. At least a portion of first section 232 and third section 236 may extend beyond the outer diameter $D_3$ 210 of the main body 202 as well. A bottom view of an exemplary locking mechanism, shown in FIG. 4, illustrates the curvature and extension of three bendable features 230 in relation to the main body 202. In an alternative arrangement, the bendable feature 230 could comprise a continuous beam rather than a beam comprising a plurality of sections.

Figure 5:
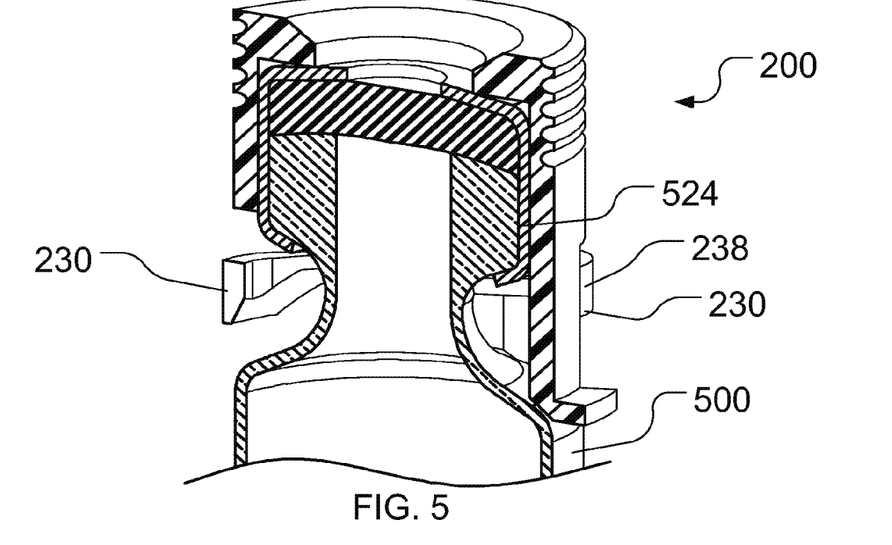
FIG. 5 illustrates a cross-sectional view of a distal cartridge portion that may be used with the locking mechanism illustrated in FIG. 3.

The locking mechanism 200 is intended for use with a cartridge, such as the cartridge 120 illustrated in FIG. 2. As illustrated in FIG. 5, the locking mechanism 200 is affixed to a cartridge 500. Cartridge 500 has a neck with a flange against which a rubber membrane is secured by a ferrule 524 beaded under the flange. The bottom of the cup-shaped cap has an opening through which part of the membrane protrudes.

FIG. 5 shows the locking mechanism 200 with bendable features 230 in the first position. As can be seen in FIG. 5, in this first position, bendable features 230 are shaped concave relative to the cartridge 500.

Figure 6:
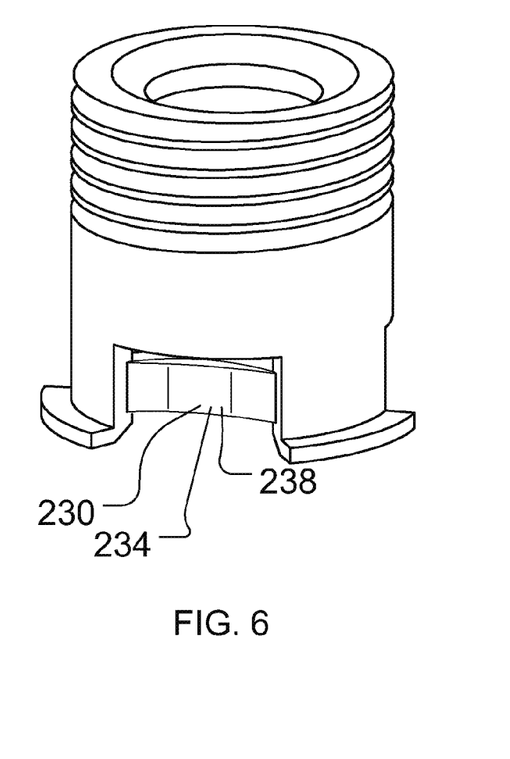
FIG. 6 illustrates a the locking mechanism illustrated in FIG. 3 in the second or final position.

Bendable feature 230 is operable to affix the locking mechanism 200 to a cartridge 500 in response to a certain mechanical input, such as during an assembly procedure or a user initiated procedure. During this mechanical input step of locking mechanism 200 to cartridge 500, bendable feature 230 is moved from the first position to a second or final position. To effect the transition from the first position to the second position, assembly tools (or perhaps a user) may press or push against the exterior surface 238 of bendable feature 230, applying pressure in the direction toward the centrally located aperture 204. The bendable feature 230 is configured such that, when pressed toward the reservoir (cartridge 500), the bendable feature 230 deforms, with the second section 234 moving toward aperture 204 until the bendable feature 230 snaps into an inverted position. This inverted position is the second position, and is shown in FIG. 6.

Figure 7:
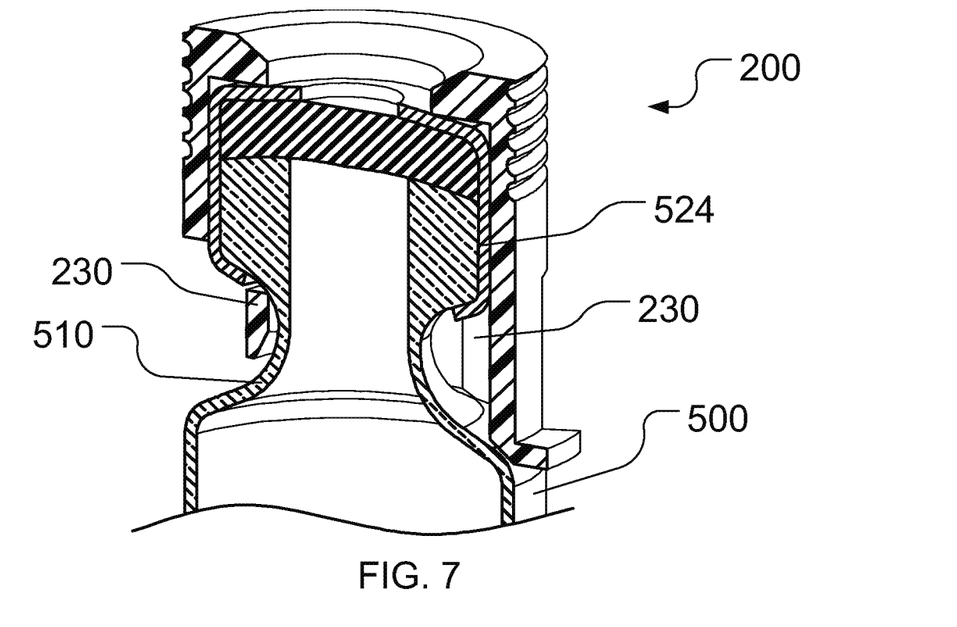
FIG. 7 illustrates the locking mechanism attached to the distal cartridge portion as illustrated in FIG. 3, with the locking mechanism in the second position.

FIG. 7 illustrates the locking mechanism 200 attached to the distal cartridge portion as shown in FIG. 3, when the bendable feature 230 is in the second position. More specifically, the locking mechanism 200 is snapped over the distal end 510 of the cartridge 500 such that it fits around the ferrule 524 of the cartridge 500. When the bendable feature 230 is in the second position, the cartridge 500 is non-removably retained within locking mechanism 200.

Figure 8:
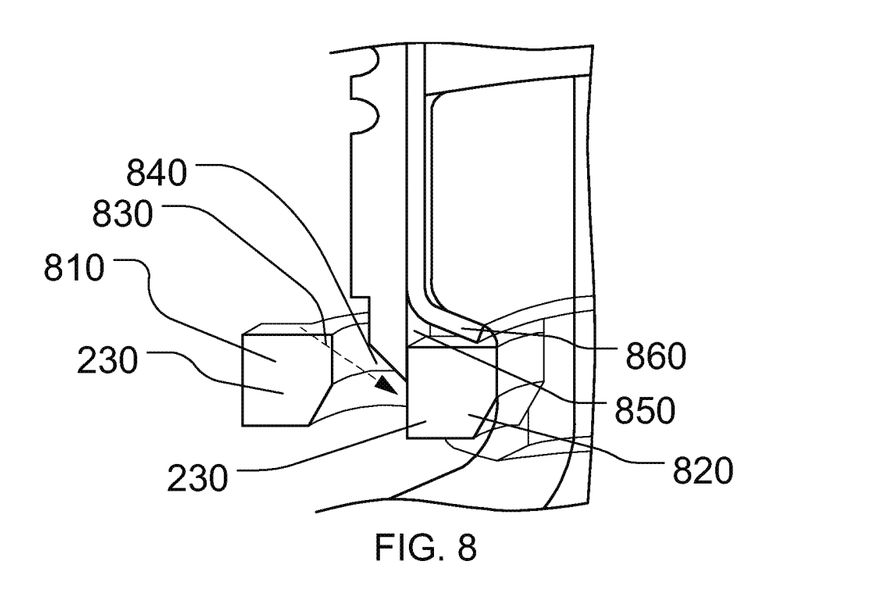
FIG. 8 illustrates a view of a portion of a bendable feature that may be present on the locking mechanism illustrated in FIG. 3, and shows the movement of the bendable feature.

FIG. 8 illustrates the movement of the bendable feature 230 from the first position 810 to the second position 820. The bendable feature 230 moves from a first position 810 along the path of arrow 830, to a second position 820. In one embodiment, as bendable feature 230 moves along the path of arrow 830, the bendable feature 230 moves past non-return feature 840 of locking mechanism 200, and rests in the second position 820, with at least part of bendable feature 230 behind ferrule 860. In the second position 820, bendable feature 230 is shown to be bound by inner surface 850 and the surface of the ferrule 860. Non-return feature 840 may vary in length, and as a consequence, the area of inner surface 850 may vary. Non-return feature 840 may, for example, be shorter (or larger) than what is shown in FIG. 8.

One advantage of using the locking mechanism 200 is that the fit of bendable feature 230 against ferrule 860 and inner surface 850 prevents the locking mechanism 200 from unwanted removal. That is, bendable feature 230 prevents unwanted removal of the locking mechanism 200 from the cartridge when a double ended needle is either attached or removed from the distal end of the locking mechanism.

Those of skill in the art will recognize that alternative geometries of this bendable feature 230 may also be used. For example, the thickness, depth, or length of any of the first section 232, second section 234, or third section 236 may be altered. As another example, the curvature of the bendable feature 230 may be increased or decreased. A change in any of these features may alter the force required to snap the bendable feature 230 toward the cartridge. Indentations may be present along the length of bendable feature 230. The indentations may weaken the structure, aiding deformation of bendable feature 230. More than one bendable feature 230 around the circumference may be provided. One advantage of having multiple bendable features 230 is that the cartridge may be retained in a plurality of locations. In addition, a plurality of locking mechanisms 200 may be provided in various colors so as to provide further differentiation or coding among various cartridges, cartridge holders, or the medicament contained within the cartridges.

Figure 9:
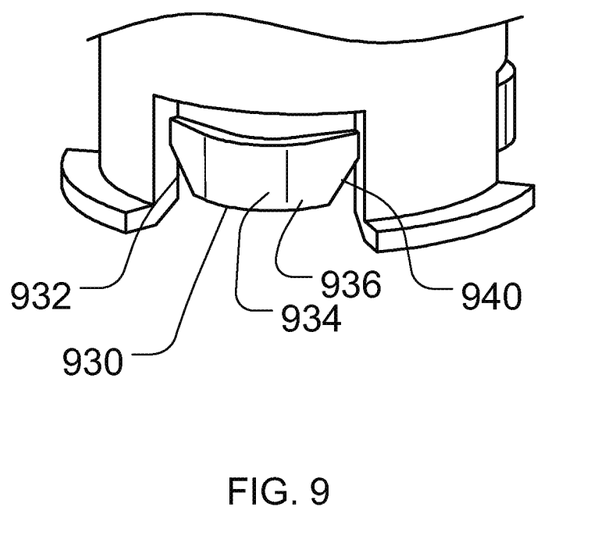
FIG. 9 illustrates an alternative arrangement of a locking mechanism.

An alternative exemplary embodiment is shown in FIG. 9. In this alternative embodiment, the bendable feature 930 comprises a first section 932, a second section 934, and a third section 936. The first section 932 and third section 936 of bendable feature 930 each have an angled edge 940, effectively reducing the material on each of first section 932 and third section 936. Reducing the material of these sections may weaken the sections such that when bendable feature 930 is in the second position, if the locking mechanism is forcibly removed from the cartridge, bendable feature 930 will be damaged and will no longer be able to retain the locking mechanism. This provides for a tamper-evident mechanism. Other tamper-evident features may also be envisioned, such as a label that may be affixed to the locking mechanism, that if manipulated, may tear or rip.

Locking mechanism may incorporate an interlocking means to prevent rotation relative to the cartridge holder. As an example, the locking mechanism may comprise protrusions with a triangular section pointed towards the distal end. As another example, rotation may be prevented by friction between the mechanism and the holder. In another alternative, retention features may clip the cartridge to the cartridge holder while still enabling for easy removal. Such retention features may comprise an interference fit, a snap fit, or a bayonet-style feature.

Figure 10:
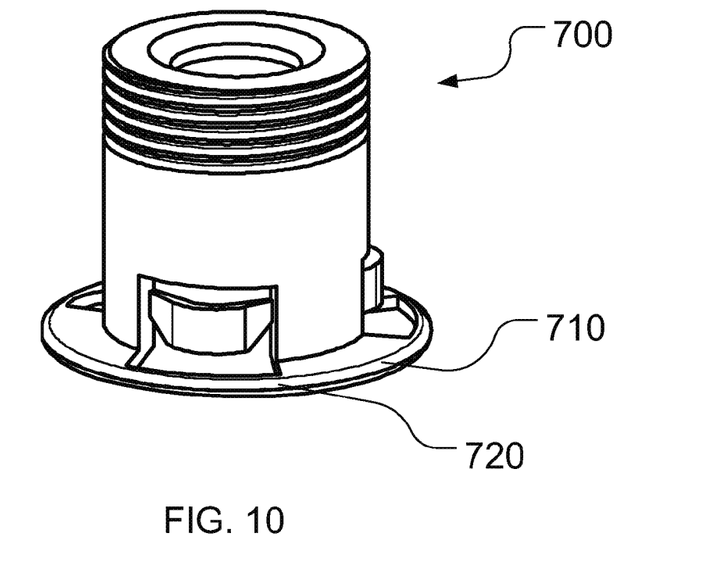
FIG. 10 illustrates an alternative arrangement of a locking mechanism.
Figure 11:
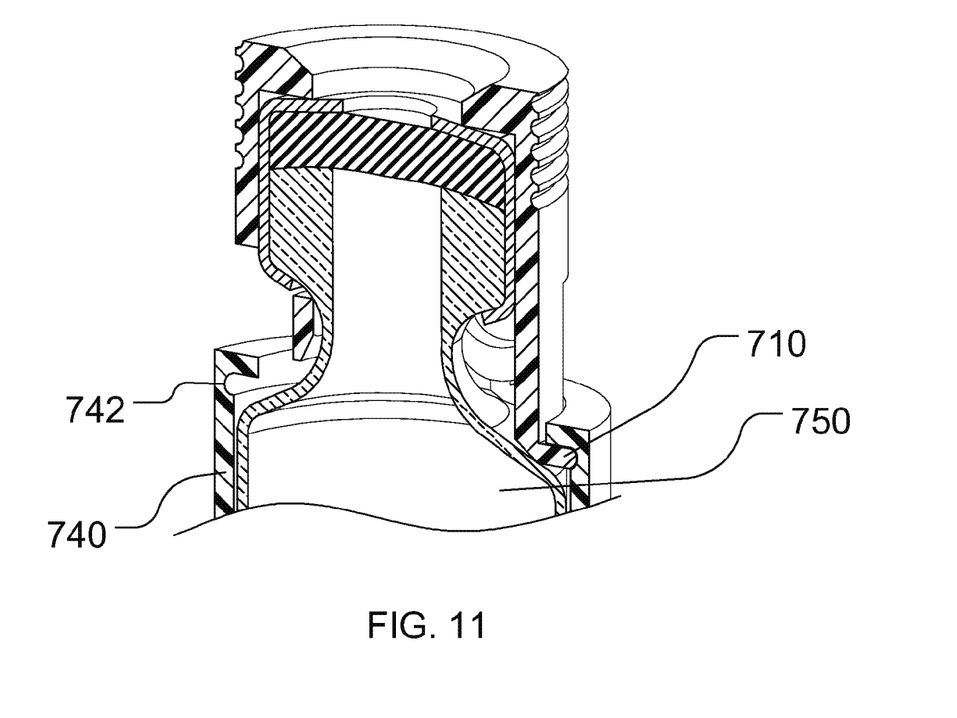
FIG. 11 illustrates a cross-sectional view of a distal cartridge portion and a distal cartridge holder portion that may be used with the locking mechanism illustrated in FIG. 10.

An exemplary retention feature is illustrated in the alternative arrangement shown in FIGS. 10 and 11. In this alternative arrangement, a locking mechanism may comprise a full flange ring. This arrangement is illustrated in FIGS. 10 and 11. FIG. 10 shows a locking mechanism 700 with a full flange ring 710. Full flange ring 710 is continuous along the entire perimeter of locking mechanism 700 near the proximal end 720 of locking mechanism 700. FIG. 11 illustrates locking mechanism 700 in place within a cartridge holder 740 that holds a cartridge 750. Cartridge holder 740 may comprise a groove or channel 742, as shown. This channel 742 may correspond with flange ring 710, such that flange ring 710 mates or fits within channel 742 when locking mechanism is mounted on cartridge 750, and resides in the second position. The full flange ring 710 may increase the strength and stiffness of the locking mechanism 700.

The proposed locking mechanism may apply to any drug delivery device, with any type of reservoir or primary pack, e.g. inhaler, pouch. The proposed locking mechanism may also comprise a coding method to the cartridge holder to prevent insertion of a cartridge into the incorrect holder. The locking mechanism may comprise a color that distinguishes the cap to be used for a specific drug.

The proposed locking mechanism results in a number of advantages. For example, the proposed locking mechanism helps to ensure that a delivery device can only be used with a medicament for which the device is intended. The locking mechanism prevents a user from removing the locking mechanism and fastening it to another cartridge. The mechanism is also tamper-evident; if removal is attempted, the locking mechanism may become damaged.

The locking mechanism also results in a low cost mechanism since the interface does not require a large number of parts and can be manufactured in a cost effective manner.

Exemplary embodiments of the present invention have been described. Those skilled in the art will understand, however, that changes and modifications may be made to these arrangements without departing from the true scope and spirit of the present invention, which is defined by the claims.

The invention claimed is:

1. A locking mechanism for attaching a cartridge within a cartridge holder, said mechanism comprising:
   a cylindrically shaped main body having an outer diameter and a centrally located aperture;
   the aperture extending from a proximal end to a distal end of the main body and the aperture configured to be placed over a sleeve or a ferrule located at a distal end of a cartridge, the cartridge including a generally tubular barrel extending from the distal end to a proximal end, the distal end of the cartridge being defined by an inwardly converging shoulder, the cartridge including a smaller diameter neck projecting distally from the shoulder of the barrel and a pierceable seal or septum securely mounted across the open distal end defined by the neck and held in place by the sleeve or ferrule;

at least one non-return feature coupled to the main body; and at least one bendable feature provided on said main body;

wherein the bendable feature comprises a first section, a second section, and a third section, the first section and the third section being affixed to the main body, wherein the bendable feature is movable from a first position, in which the bendable feature has an arc shape such that at least a portion of the second section of the bendable feature extends beyond an outer diameter of the main body, to a second position, the portion moving toward the aperture and deforming until the bendable feature moves past the non-return feature and snaps into an inverted position behind the sleeve or ferrule in the second position, and wherein in the second position, at least a portion of the bendable feature is provided to retain the cartridge within the locking mechanism and the bendable feature is held in the second position by the non-return feature.

2. The locking mechanism of claim 1, wherein said main body comprises a flange or flange ring that extends along at least a portion of the perimeter of said main body.

3. The locking mechanism of claim 1, wherein a thread is provided on the main body and configured for receiving a threaded needle hub.

4. The locking mechanism of claim 1, further comprising a retention feature, wherein said retention feature comprises a flange or flange ring, which extends from said main body.

5. A drug delivery system comprising:
a drug delivery device comprising a dose setting member;
a cartridge holder, wherein said cartridge holder is secured to said dose setting member;
a cartridge contained within said cartridge holder; and
a locking mechanism according to claim 1, affixed to said cartridge.

6. The drug delivery system of claim 5, wherein said main body comprises a flange or flange ring that extends along at least a portion of the perimeter of said main body.

7. The drug delivery system of claim 5, wherein an outer surface of the axially extending wall of the main body is provided with an outer thread.

8. The drug delivery system of claim 5, wherein said cartridge holder is removably secured to said dose setting member.

9. The drug delivery system of claim 5, wherein said cartridge is removably contained within said cartridge holder.

10. The drug delivery system of claim 5, wherein said drug delivery device comprises a reusable drug delivery device.

11. The drug delivery system of claim 5, wherein said dose setting member comprises a rotating piston rod for expelling a set dose from said cartridge.

* * * * *